United States Patent [19]

Segal

[11] Patent Number: 4,856,529
[45] Date of Patent: Aug. 15, 1989

[54] ULTRASONIC PULMONARY ARTERY CATHETER AND METHOD

[75] Inventor: Jerome Segal, Palo Alto, Calif.

[73] Assignee: Cardiometrics, Inc., Moutain View, Calif.

[21] Appl. No.: 11,615

[22] Filed: Feb. 6, 1987

Related U.S. Application Data

[60] Continuation-in-part of Ser. No. 2,585, Jan. 12, 1987, abandoned, which is a division of Ser. No. 737,650, May 24, 1985, Pat. No. 4,733,669.

[51] Int. Cl.⁴ .............................................. A61B 8/00
[52] U.S. Cl. ........................... 128/661.08; 128/661.09; 128/662.04; 128/673
[58] Field of Search ............... 128/663, 667, 673, 713, 128/657, 658, 772, 661.07–661.10; 604/280, 281, 264, 96, 102

[56] References Cited

U.S. PATENT DOCUMENTS

| | | | |
|---|---|---|---|
| 3,554,030 | 1/1971 | Peronneau | 128/663 |
| 3,566,682 | 3/1971 | Winkler, Jr. | 73/152 |
| 3,729,008 | 4/1973 | Berkovits | 604/281 |
| 3,773,037 | 11/1973 | Kolin . | |
| 4,033,331 | 7/1977 | Guss et al. | 604/281 |
| 4,354,500 | 10/1982 | Culley et al. | 128/663 |
| 4,375,818 | 3/1983 | Suwaki et al. | 128/4 |
| 4,545,244 | 10/1985 | Yasuda et al. | 73/861.25 |
| 4,554,929 | 11/1985 | Samson et al. | 128/772 |
| 4,582,067 | 4/1986 | Silverstein et al. | 128/663 |
| 4,584,874 | 4/1986 | Ruhovets | 73/152 |
| 4,637,401 | 1/1987 | Johnston | 128/663 |

FOREIGN PATENT DOCUMENTS

| | | | |
|---|---|---|---|
| 0132344 | 1/1985 | European Pat. Off. . | |
| 2758039 | 7/1979 | Fed. Rep. of Germany | 128/662 |
| 2424733 | 1/1980 | France | 128/663 |

OTHER PUBLICATIONS

Lavandier et al. "Non Invasive Aortic Blood Flow Measurement Using An Intraesophageal Probe", Ultrasound in Med. & Biol. vol. 11 No. 3 pp. 451–460 May/Jun. 1985.
Martin et al., "An Ultrasonic Catheter For Intravascular Measurement of Blood Flow", Transactions on Sonics and Ultrasonics, vol. SU-27 No. 6 Nov. 1980 pp. 277–286.
Allen et al., "Integrated Circuits for a Bidirectional Implantable Pulsed Doppler Ultrasonic Blood Flowmeter", IEEE Journal of Solid State Circuits Vol. SC-13 No. 6. Dec. 1978 pp. 853–856.

*Primary Examiner*—Ruth S. Smith
*Attorney, Agent, or Firm*—Flehr, Hohbach, Test, Albritton & Herbert

[57] ABSTRACT

Catheter for making measurements in a vessel defined by a wall carrying a fluid comprising an elongate flexible tubular member having a plurality of lumens extending therethrough and having proximal and distal extremities. An inflatable balloon is carried by the distal extremity of the tubular member and has the interior of the balloon in communication with one of the lumens in the flexible tubular member. The tubular member has at least one predetermined bend therein adjacent the distal extremity of the tubular member. A transducer is carried by the tubular member in the region of the predetermined bend. Conductors are connected to the transducer and are carried by the tubular member and extends through one of the lumens in the tubular member to the proximal extremity of the tubular member. The tubular member has an opening in the distal extremity distal of the balloon in communication with one of the lumens in the tubular member. The tubular member has another opening proximal of the balloon and is in communication with another lumen. A straightening wire is carried by the tubular member for straightening the predetermined bend when it is extended through the predetermined bend to facilitate insertion of the catheter into the vessel and for permitting the tubular member to assume the predetermined bend within in the vessel when it is retracted so that it does not extend through the predetermined bend so that a portion of the bend engages the wall of the vessel to position the transducer so that radiation emitted thereby passes through the fluid in the vessel.

10 Claims, 4 Drawing Sheets

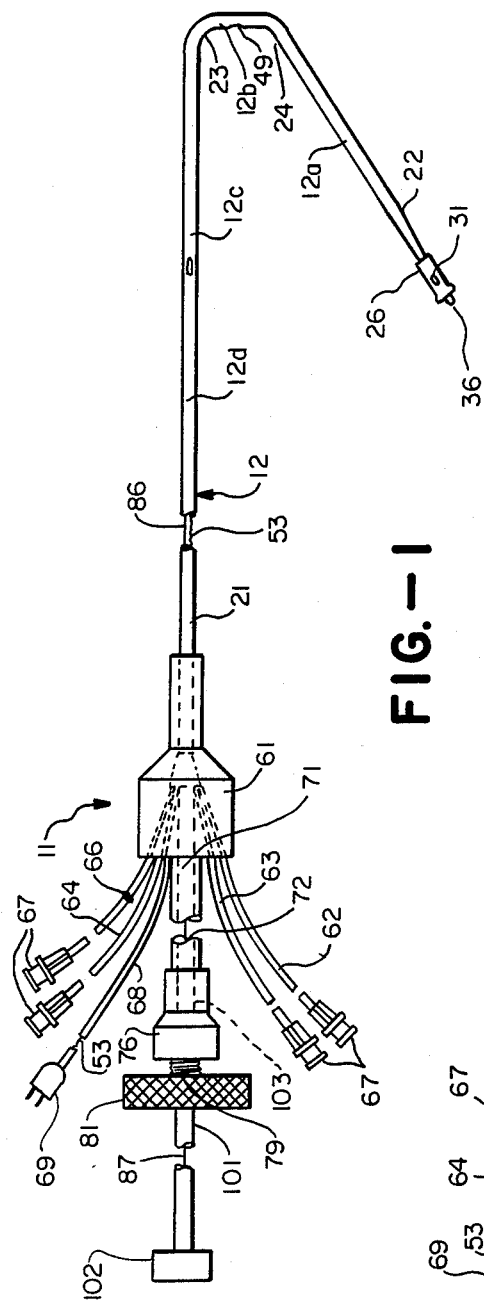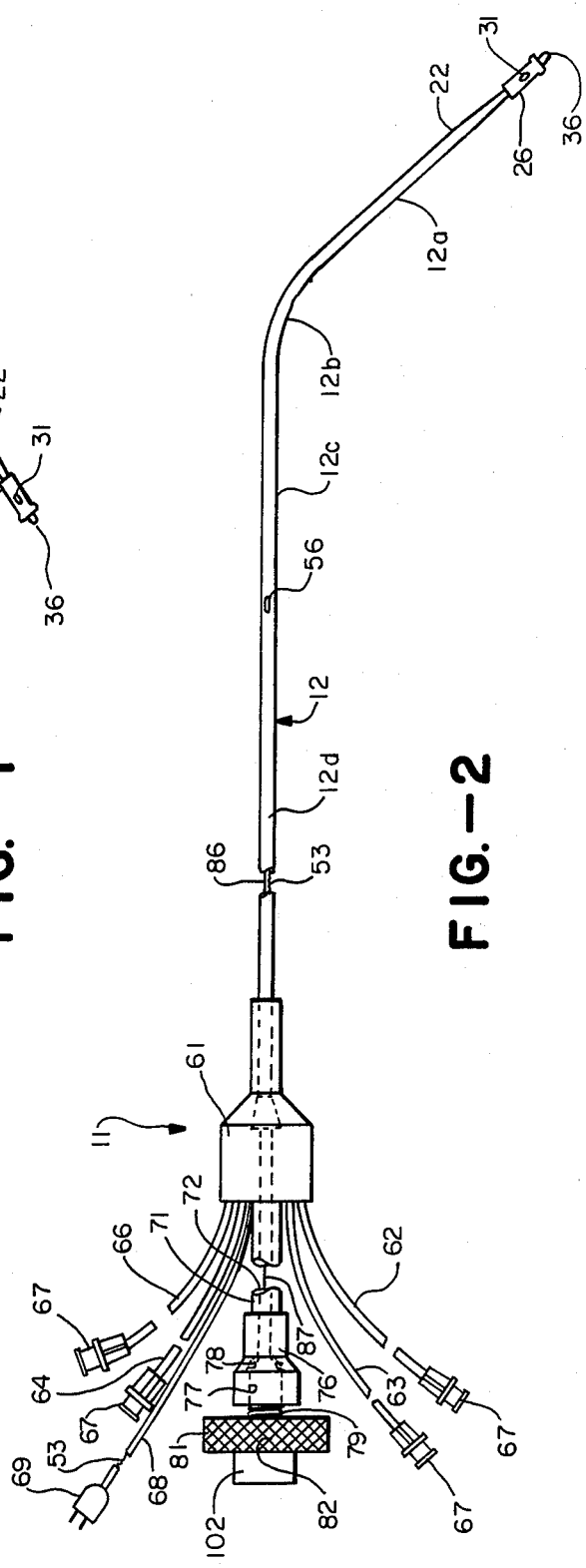

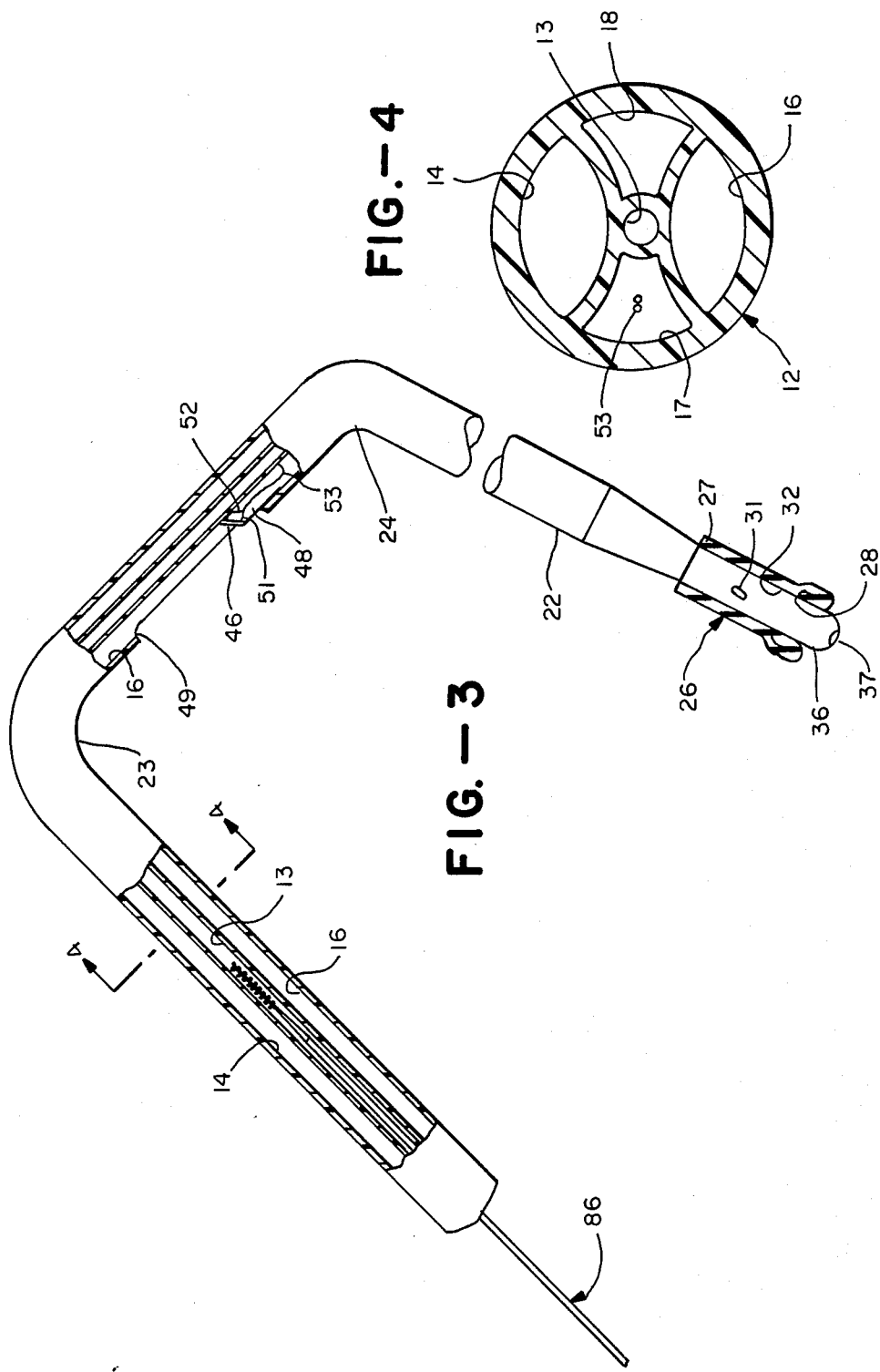

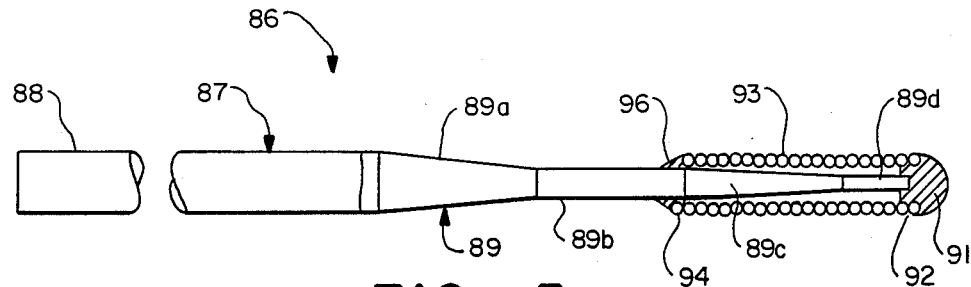
FIG.—5
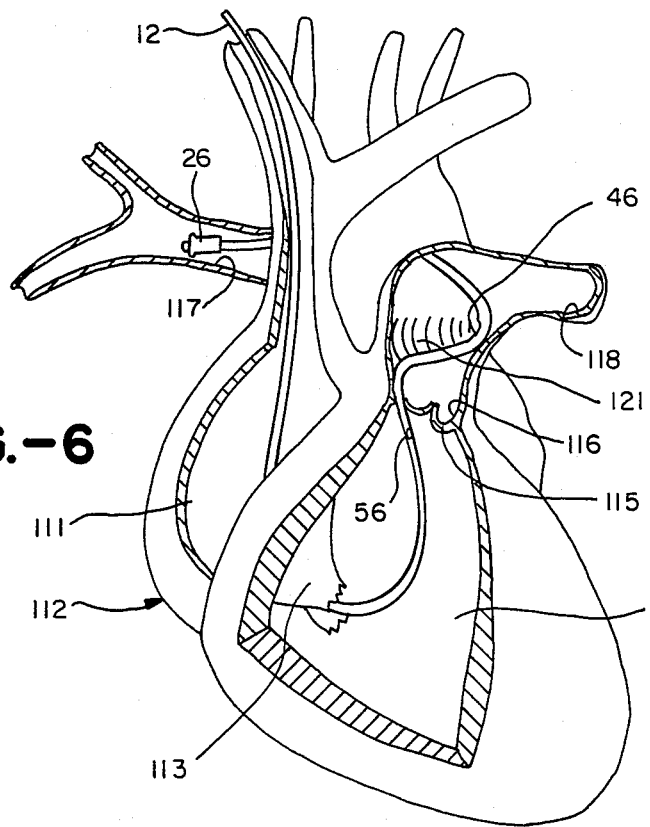
FIG.—6
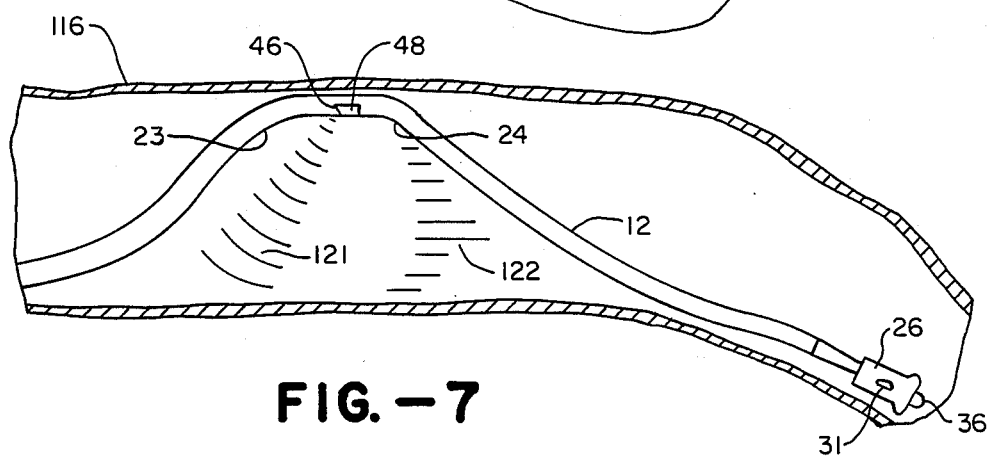
FIG.—7

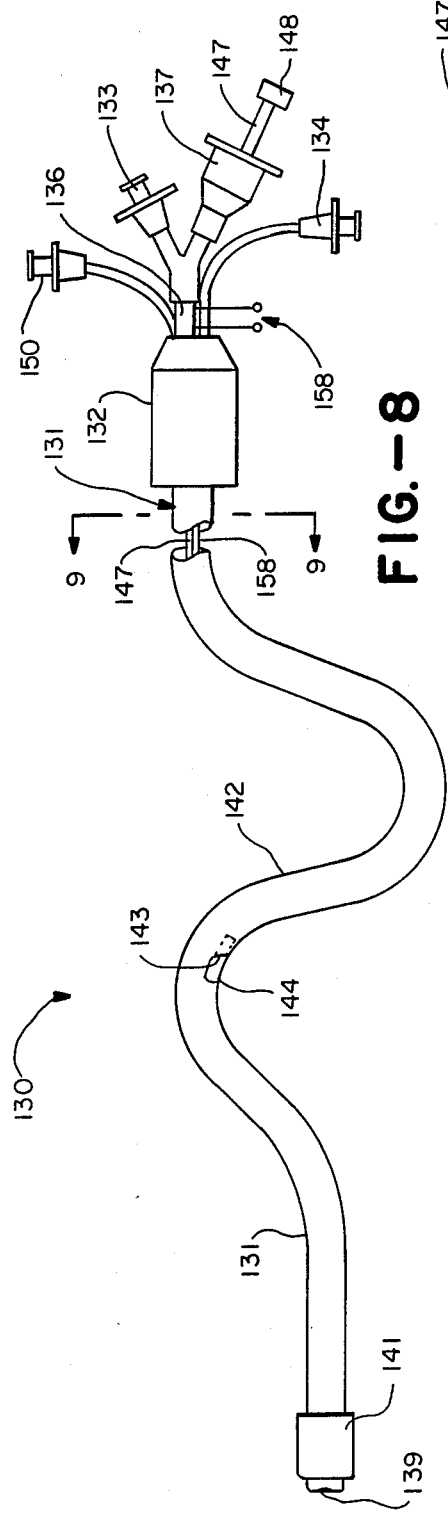
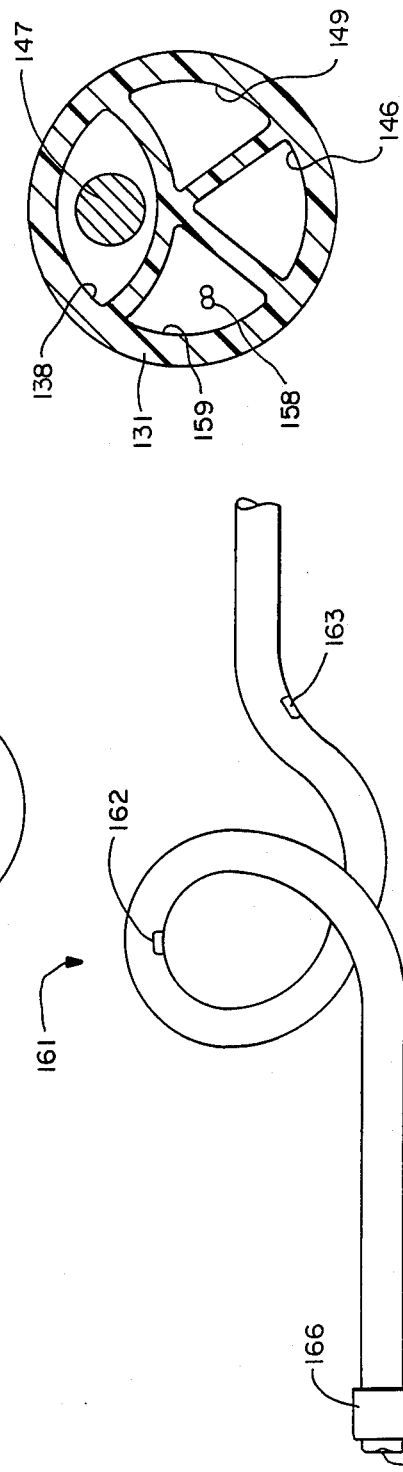
FIG.—8
FIG.—9
FIG.—10

ULTRASONIC PULMONARY ARTERY CATHETER AND METHOD

This invention is a continuation-in-part of application Ser. No. 002,585, filed on Jan. 12, 1987 now abandoned, which is a division of application Ser. No. 737,650, filed May 24, 1985 now U.S. Pat. No. 4,733,669.

This invention relates to ultrasonic arterial catheters and methods for use therein and, in particular, ultrasonic pulmonary artery catheters and methods adapted to be utilized for measuring instantaneous blood flow.

Catheters have heretofore been utilized for making pressure measurements and for measuring cardiac output. Cardiac output in man typically has been ascertained by the Fick method, by a dye indicator dilution method and by a thermal indicator dilution method, none of which make possible the measurement of continuous instantaneous cardiac output. There is therefore a need for a new and improved catheter which can be utilized for measuring instantaneous blood flow in the pulmonary artery and other vessels.

In general, it is an object of the present invention to provide an ultrasonic pulmonary artery catheter and method which can be utilized for continuous monitoring of cardiac output.

Another object of the invention is to provide a catheter and method of the above character which utilizes ultrasonic energy and in which it is possible to direct the ultrasonic energy in a blood vessel with substantial precision.

Another object of the invention is to provide a catheter of the above character which is provided with a preformed shape which can be utilized to place an ultrasonic transducer in a position with respect to the wall of the blood vessel to provide aiming of the ultrasound beam through the fluid in the vessel.

Another object of the invention is to provide a catheter and method of the above character in which it is possible to obtain ultrasonic beam penetration through a central axis of the vessel to thereby make it possible to obtain an accurate measurement of velocity and surface area.

Another object of the invention is to provide a catheter and method of the above character which utilizes the Doppler principle for making instantaneous cardiac output measurements.

Another object of the invention is to provide a catheter and method of the above character which makes it possible to accurately calculate the quantitative flow of blood through a blood vessel.

Another object of the invention is to provide a catheter and method of the above character in which the precise orientation of the transducer with respect to blood flow in the vessel is known.

Another object of the invention is to provide a catheter and method of the above character which makes it possible to positively ascertain when the transducer is located in the main pulmonary artery.

Additional objects and features of the invention will appear from the following description in which the preferred embodiments are set forth in detail in conjunction with the accompanying drawings.

FIG. 1 is a side elevational view of ultrasonic pulmonary artery catheter incorporating the present invention showing the same with the straightening wire retracted.

FIG. 2 is a view similar to FIG. 1 but showing the catheter with the straightening wire extended.

FIG. 3 is an enlarged portion of a distal extremity of the catheter shown in FIG. 1 with certain portions broken away.

FIG. 4 is an enlarged cross sectional view taken along the line 4—4 of FIG. 3.

FIG. 5 is a side elevational view of the straightening wire used in the catheter shown in FIG. 2.

FIG. 6 is a diagrammatic illustration of the manner in which the catheter is utilized in a human heart to measure the quantitative blood flow through the pulmonary artery.

FIG. 7 is an illustration showing the manner in which blood flow can be calculated utilizing a Doppler effect ultrasonic transducer in accordance with the present invention.

FIG. 8 is another embodiment of the catheter incorporating the present invention which is shown in the earlier filed application Ser. No. 737,650, filed May 24, 1985.

FIG. 9 is an enlarged cross-sectional view taken along the line 9—9 of FIG. 8.

FIG. 10 is a side elevational view of still another embodiment of the catheter of the present invention which was shown in the earlier filed application Ser. No. 737,650, filed May 24, 1985.

In general, the catheter of the present invention is comprised of an elongate flexible tubular member or body having a plurality of lumens extending therethrough. The tubular member has proximal and distal extremities. An inflatable balloon is carried by the distal extremity of the tubular member and has its interior in communication with one of the lumens in the flexible tubular member. The tubular member is provided with a predetermined bend therein adjacent the distal extremity of the tubular member. A transducer is carried by the tubular member in the region of a predetermined bend. Conductive means is connected to the transducer and is carried by the tubular member and extends through one of the lumens in the tubular member to the proximal extremity of the tubular member. The tubular member has an opening in the distal extremity thereof distal of the balloon and in communication with one of the lumens in the tubular member The tubular member has an additional opening proximal of the balloon and in communication with another lumen in the tubular member. Means is carried by the tubular member for straightening the predetermined bend in the tubular member to facilitate insertion of the catheter into a vessel body having a liquid flowing therein.

More in particular, the catheter 11 of the present invention consists of a flexible elongate tubular member or body 12 formed of a suitable plastic such as polyurethane having a suitable outside diameter such as 0.090 inches and a length of approximately 50 to 100 centimeters and preferably approximately 90 centimeters. The distal extremity of the tubular member is of slightly reduced diameter of approximately 0.072 inches. This portion of reduced diameter has a suitable length as, for example, a length of 1½ centimeters. The flexible elongate tubular member 12 is provided with a plurality of lumens extending therethrough and as shown, particularly in FIG. 4, namely lumens 13, 14, 16, 17 and 18. The lumen 13 can be identified as a straightening wire lumen. The lumen 14 can be identified as a transducer and a proximal pressure lumen and the lumen 16 can be identified as the distal pressure lumen. The lumen 17 can be identified as the balloon and transducer wire lumen and lumen 18 as the right ventricle pressure lumen. If desired, fewer or lesser lumens can be provided in the flexible elongate tubular member. Although the lumens 13, 14, 16, 17 and 18 all have been shown as having a predetermined configuration, it should be appreciated that different configurations of lumens can be utilized if desired. The flexible elongate member 12 is provided with proximal and distal extremities 21 and 22.

The flexible elongate tubular member 12 is provided with one or more predetermined bends therein. Thus, by way of example, there are provided two predetermined bends 23 and 24. The bends 23 and 24 can subtend suitable angles, as for example, the bend 23 can subtend an angle of approximately 90°, whereas the bend 24 can subtend an angle of approximately 65°. The predetermined bends can be placed in the flexible tubular member 12 by placing in molds the portions of the flexible tubular member in which it is desired to place the bends and heating the molds to suitable temperature and then permitting the flexible elongate tubular member to cool within the molds so that the bends formed therein during heating are retained as the predetermined bends hereinbefore described.

An inflatable balloon 26 is carried by the distal extremity 22 of the flexible elongate tubular member 12. The balloon 26 is formed of a suitable material such as a latex cylindrical sleeve having a wall thickness of approximately 0.001 inches and having proximal and distal extremities 27 and 28. The distal extremity 28 is secured to the exterior surface of the flexible tubular member 12 by suitable means such as an adhesive with the proximal extremity 27 extending forwardly of the tubular member 12. The proximal extremity 27 is the folded over the tubular member 12 as shown in FIG. 3 and then secured to the tubular member 12 by suitable means such as an adhesive. A hole or opening 31 is provided in the tubular member 12 and opens into the interior 32 of the balloon and also is in communication with the balloon inflation lumen 17. A tip 36 of a suitable relatively soft pliable plastic is secured to the distal extremity of the tubular member 12 by suitable means such as an adhesive. Alternatively, the tip 36 can be formed integral with the distal extremity of the tubular member 12 by extruding that portion of the tubular member 12 to a small diameter. The tip 36 is provided with an opening 37 which is in communication with the distal pressure lumen 16.

An ultrasonic transducer 46 of a suitable conventional type such as one of lead titanate zirconate with silver electrodes is carried by the tubular member 12 and is of a size so that it can readily fit within the transducer and pulmonary artery pressure lumen 14.

The ultrasonic transducer 46 is in the form of a relatively thin planar chip which is mounted at a predetermined angle, as for example, an angle of approximately 45° on an insulating block 48 of a suitable material such as an epoxy impregnated with tungsten oxide. The flexible elongate member 12 is provided with an elongate slot 49 opening into the transducer and pulmonary artery pressure lumen 14. The slot 49 makes it possible to insert the block 48 with the transducer carried thereby into the lumen 14 and to secure the same therein in a predetermined position, such as by means of an adhesive. Leads 51 and 52 are carried by the block 48 and are secured to the silver electrodes of the ultrasonic transducer 46. The leads 51 and 52 extend forwardly in the block 48 and are intertwined to provide an intertwined lead 53 which extends rearwardly from the block 48 and then through the balloon and transducer wire lumen 17.

Another opening 56 is provided in the flexible elongate tubular member 12 proximal of the opening or slot 49 by a distance of approximately five centimeters and is in communication with the right ventricle pressure lumen 18. The distance of five centimeters should correspond approximately to the length of the main pulmonary artery in man.

A manifold 61 of a suitable material such as plastic is mounted on the proximal extremity 21 of the tubular member 12. The manifold 61 carries a plurality of small elongate tubular members 62, 63, 64, 66 and 68. The distal extremities of the members 62, 63, 64 and 66 are inserted into the lumens 14, 16, 17 and 18, respectively and are sealed therein and also molded into the manifold 61. Luer-type fittings 67 are also provided on the proximal extremities of the members 62, 63, 64 and 66. Elongate tubular member 64 containing intertwined wires 53, branches into tubular member 68 which carries the wires 53. The wires 53 are connected to an electrical connector 69 mounted onto the proximal extremity of the tubular member 68.

A rigid tubular sleeve 71 has its distal extremity mounted within the manifold 61 and has a flow passage 72 extending therethrough in communication with the central lumen 13 in the tubular member 12. The sleeve 71 can be formed of a suitable material of stainless steel and can have a suitable length such as approximately 10 centimeters. A fitting 76 is carried by the proximal extremity of the sleeve 71 and is provided with a flow passage 77 in communication with the passage 72. An O-ring 78 is seated in the fitting 76 and is adapted to be engaged by a threaded boss 79 threadedly mounted in the fitting 76. The boss 79 is provided with a knurled knob 81 to facilitate rotation of the same. The boss 79 and the knob 81 are provided with a bore 82 extending therethrough which is in communication with the flow passage 77.

A straightening wire or pliable filament 86 is provided for use with the catheter 11 shown in FIGS. 1, 2 and 3 and consists of a core wire 87 formed of a suitable material such as stainless steel and having a suitable length, as for example, 120 centimeters. It can have a suitable diameter as, for example, 0.014 inches. If desired, a larger diameter core wire can be utilized. The core wire 87 is provided with proximal and distal extremities 88 and 89. The distal extremity 89 is provided with multiple tapers to provide increased flexibility for the distal extremity. Thus, as shown, with a distal extremity of approximately 5 centimeters in length, a tapered portion 89a can be provided in which the diameter is reduced from 0.014 inches to 0.008 inches. Also provided is a straight cylindrical portion 89b of a length of approximately 1 centimeter and a diameter of 0.008 inches, a tapered portion 89c in which the diameter is reduced from 0.008 inches to 0.003 inches and a flattened portion 89d having a width of approximately 0.003 inches and a thickness of approximately 0.001 inches. The portion 89d terminates in a rounded protrusion 91 formed of a suitable material such as a tin silver solder. The protrusion 91 is also bonded to the distal extremity 92 of a coil spring 93. The proximal extremity 94 of the coil spring 93 is secured to the cylindrical portion 89b of the tapered portion 89 by suitable means such as solder 96. The coil spring can be formed of a suitable material such as stainless steel spring wire having a diameter of 0.01 inches and in which the outside diameter of the coil has a suitable diameter as, for example, 0.0012 inches.

The proximal extremity 88 of the core wire 87 extends through a rigid hypodermic tube 101 of a suitable diameter such as 0.005 inches and having a length of approximately 10 centimeters. The proximal extremity of the hypodermic tube 101 and of the core wire 87 is secured to a knob 102. A mechanical stop in the form of a sleeve formed of suitable material such as a rubber material is provided on the distal extremity of the hypodermic tube 101 and engages the boss 79 to prevent retraction of the straightening wire 86. The straightening wire 86 is adapted to be advanced through the straightening wire lumen 13 for straightening the catheter 11 as hereinafter described.

Operation and use of the ultrasonic pulmonary artery catheter may now be briefly described as follows. In preparation of the catheter 11 for insertion into the pulmonary artery of a human patient, the distal extremity of the catheter 11 is straightened by grasping the knob 102 and pushing the same to advance the straightening wire into the bends 23 and 24 while pulling gently on the distal extremity of the catheter. The distal extremity of the straightening wire 87 readily negotiates these bends because of the relatively flexible spring tip provided on the straightening wire and also because of the fact that a rounded protrusion 91 is carried by the distal extremity of the spring. Great flexibility is provided by the various tapers provided in the distal extremity 89 of the straightening wire 87. As the flexible distal extremity negotiates the turns, the stiffer portions of the straightening wire enter the bends 23 and 24 to straighten them so that the catheter 11 assumes the general conformation as shown in FIG. 2.

With the catheter in the conformation shown in FIG. 2, the catheter can be readily inserted into the appropriate vessel into the patient and advanced in a conventional manner into the desired position in the patient's vessel.

Let it be assumed it is desired to obtain a continuous cardiac output by measuring the flow of blood in the pulmonary artery. The catheter 11 is connected to appropriate monitoring equipment (not shown). The catheter 11 is then introduced by percutaneous technique through a suitable needle or sheath. The catheter is gently advanced until its tip has been advanced into the superior or inferior vena cava or the right atrium 111 as shown in FIG. 6. At this point, the balloon 26 is inflated to an appropriate volume as, for example, 1.5 cc by the use of a suitable gas such as carbon dioxide. As soon as the balloon has been inflated, the balloon will travel through the right atrium 111 of the patient's heart 112 (see FIG. 6). Then it will travel through the tricuspid valve 113 and into the right ventricle 114, through the pulmonic valve 115, and thence into the main pulmonary artery 116 and then thereafter to assume a pulmonary wedge position in the pulmonary artery beyond its bifurcation into right and left pulmonary artery branches, 117 and 118, respectively. Pulmonary artery pressures will be observed as soon as the balloon and transducer lumen slot 49 passes through the pulmonic valve 115. The catheter 11 is permitted to be advanced with the balloon 26 inflated until the distal pressure lumen indicates that pulmonary capillary wedge position has been reached. At this point simultaneous pulmonary capillary wedge pressure, pulmonary artery pressure and right ventricular pressures can be ascertained using the distal, transducer, and right ventricular pressure lumens, 14, 16, and 18, respectively. Once these pressures have been recorded, the balloon 26 can be deflated by withdrawing the carbon dioxide and the catheter can be slowly withdrawn towards a previously recorded transition point until a right ventricular pressure trace appears via the right ventricular lumen 18 and a pulmonary artery pressure trace appears via the transducer lumen 14. This procedure confirms the position of the transducer within the main pulmonary artery. Placement of the transducer 46 in the main pulmonary artery 116 is critical for measurement of total cardiac output since the entire cardiac output is ejected only through the main pulmonary artery 116. Measurement of flow in either the right pulmonary artery 117 or left pulmonary artery 118 by advancing the transducers too far distally would result in significant underestimation of total cardiac output. Simultaneous observation of pressures from transducer slot 49 and right ventricular opening 56 assures placement of the transducer 46 in the main pulmonary artery 116. This is accomplished by placement of right ventricular hole 56 a distance of 5 cm proximal from transducer slot 49 (the approximate length of the main pulmonary artery in an adult human being). Observation of a pulmonary artery pressure waveform via right ventricular hole 56 assures the operator that transducer 46 cannot be more than 5 cm beyond the pulmonic valve 115 and thence in the main pulmonary artery 116. Should transducer 46 and transducer slot 49 advance beyond the bifurcation to a branch 117 or 118 of the pulmonary artery, pulmonary artery waveforms will be observed, emanating from both slot 49 and hole 56, indicating that catheter 12 need be withdrawn slightly to place transducer 46 within the main pulmonary artery 116. Once positioning of transducer 46 in the pulmonary artery is confirmed as above, the straightening wire 86 can be retracted by grasping the top of knob 102 and withdrawing tubing 101 and straightening wire 87 until the threaded boss 79 is reached. The boss 79 serves as a stop or abutment member when this has occurred, the straightening wire 86 is withdrawn from the bends 23 and 24 to permit the distal extremity of the catheter to assume its preformed shape in the manner shown in FIG. 6 in which that portion of the flexible elongate element 12 carrying the transducer 46 is positioned against the one wall of the pulmonary artery. Restoration of the shapes or conformation of the bends 23 and 24 in the elongate element 12 results in wedging of the transducer 46 tightly against one wall of the blood vessel. Circular symmetry of the cross section of the pulmonary artery 116 assures that transducer 46 is positioned so that it is facing in a direction which extends through the central flow axis of the pulmonary artery.

Thereafter in a conventional manner, electrical energy is supplied from circuitry (not shown) through the intertwined leads 53 to the ultrasonic transducer 46 to cause the same to emit a series of short bursts of ultrasound. These series of short bursts are represented by the wave-like forms 121 shown in FIG. 6. These short bursts of ultrasound are reflected by the red blood cells within the flowing blood in the pulmonary artery. These reflected waves or signals are sampled at a series of intervals corresponding to round trip transit times between the transducer 46 and the various sample volumes within the blood vessel. The blood flow velocity of each sample volume can then be determined by detecting the Doppler frequency shift of the transmitted signal using well known techniques. In addition, the direction of blood flow can be determined by using two reference ultrasound signals that are generated at 90° out of phase with each other.

Utilizing such techniques it is possible to map a one dimensional velocity profile (see FIG. 7) by establishing a number of individual range gates 122 and spanning the diameter of the blood vessel in which the transducer is positioned.

The vessel diameter can be readily determined utilizing automatic diameter detection system of the type well known to those skilled in the art. Such systems which provide dynamic range-gating and diameter detection utilize Doppler shifted ultrasonic power within three sample gates such as one centered on the distal vessel wall, one near the vessel wall and one within the center of the vessel. A feedback loop adjusts gate positions so that reflected Doppler power from the far wall is a preset fraction of the Doppler power obtained from a sample volume located entirely within the central vessel lumen. The vessel diameter is then determined by continuously detecting the delay transit time to the far sample gate as it is adjusted to remain centered on the far wall. Instantaneous flow is calculated from the instantaneous space average velocity and instantaneous diameter using formulas well known to those skilled in the art.

The balloon 26 may again be reinflated with the 0.15 cc of carbon dioxide in order to obtain simultaneous wedge pressure (via the distal lumen 16), pulmonary artery pressure (via the transducer lumen 14), right ventricular pressure (via the right ventricular lumen 18) and continuous cardiac output.

After the desired measurements of blood flow have been made, the catheter can be removed by again reintroducing the straightening wire 86 into the bends 23 and 24 to substantially straighten the distal extremity of the catheter. Thereafter, the catheter can be removed by withdrawing it from the vessel of the patient.

In accordance with the present invention, it can be seen that the catheter 11 has been preshaped to ensure a proper orientation of the ultrasonic transducer 46 which is carried by the distal extremity of the catheter 11. The preformed shape makes it possible to position the ultrasonic transducer 46 precisely within the blood vessel so that the ultrasound pulses emitted therefrom pass directly through the center of the vessel or lumen to make it possible to ensure accurate and continuous cardiac output monitoring. As pointed out previously, during insertion of the catheter, continuous pressure monitoring of precisely spaced transducer slot 49 and right ventricular hole 56 via transducer lumen 14 and right ventricular lumen 18 respectively assures that the transducer 46 is located within the main pulmonary artery such that accurate cardiac output can be measured. Once the catheter has been properly positioned, the straightening wire 86 can be retracted permitting the catheter, with its preformed distal extremity to properly orient itself in a stable position within the pulmonary artery and to at the same time, position the ultrasonic transducer 46 so that it emits pulses in a direction which pass diametrically through the vessel. Continuous cardiac output can then be displayed on an appropriate monitor (not shown).

Even though the distal extremity of the catheter 11 has been provided with preformed bends 23 and 24, these bends can be readily straightened by use of a straightening wire or pliable filament 86 to facilitate insertion and removal of the catheter from the patient's vessel.

The catheter of the present invention makes it possible to obtain proper orientation of the ultrasonic transducer against a vessel wall with the ultrasonic pulses being emitted therefrom passing through a central diameter and longitudinal axis of the vessel to make it possible to obtain accurate measurements of velocity and surface area using the well-known Doppler principle. Since the angulation of the ultrasonic transducer to the catheter body and the blood vessel are known, accurate quantitative flow may be calculated.

An additional embodiment of a catheter 130 of the present invention is shown in FIG. 8 as described in pending application Ser. No. 737,650 filed on May 24, 1985. FIG. 9 is an enlarged cross-sectional view of catheter 130 taken along the line 9—9 of FIG. 8. This catheter 130 is comprised of a flexible elongate member or body 131 having a proximal end fitting 132 which has a number of ports, including two pressure ports 133 and 134. Pressure port 133 is coupled to an output tube 136 which is also coupled to port 137 and to a lumen 138 which is one of four lumens provided in the tubular elongate member or body 131. The lumen 138 opens to ambient through a hole 139 at its distal extremity in order to provide a pressure reading distal of a balloon 141. The distal extremity of the catheter tubular member 131 is preformed into an S-shaped curve 142 as indicated in FIG. 8. A Doppler crystal transducer 143 is located at the underside of the curve at approximately the apex thereof within a slot 144 opening into another lumen 146 in the element 131. The lumen 146 is coupled to the pressure port 134 permitting pressure monitoring of slot 144 in proximity of the transducer 143. A straightening or guide wire 147 which is provided with a knob 148 can be extended through lumen 138 from the port 137 to distal extremity of catheter in a manner previously described. The guide wire 147 as it is advanced through the lumen 138 serves to straighten out the S-curve 142 of the tubular member 131 for insertion into the vessel of the patient. The guide wire 147 must be of sufficient strength to straighten the catheter but of sufficient flexibility to allow for ease of insertion of the catheter. Once the distal extremity of the tubular member 131 is in the proper position, guide wire 145 is retracted, allowing the tubular member 131 to assume its preformed shape. In this preformed shape, the portion of the catheter proximate the transducer 143 will be wedged against a side wall of the vessel as, for example, in the pulmonary artery of the heart. The balloon 141 can then be inflated through a lumen 149 connected to a port 150 to separate the two pressure holes 139 and 144 thereby blocking pressures from the right side of the heart and exposing hole 139 to pulmonary venous pressures which in turn reflect pressures on the left side of the heart while slot 144 will give pressure readings from the pulmonary artery and the right side of the heart. Wires 158 are provided which are connected to the transducer 142 and extend through a lumen 159.

Another embodiment of the invention which was also described in the earlier filed application Ser. No. 737,650, filed on May 24, 1985 is shown in FIG. 10. In this embodiment, the catheter 161 is preformed into a spiral loop shape, as shown. A Doppler crystal 162 is located at the apex of the loop. When in place in an artery, transducer 162 will be at the portion of the catheter wedged against the side wall of the artery. Because the loop is in a spiral, the portion of the loop opposite the transducer 162 will not be in line with the transducer and thus will not interfere with the velocity measurement. This embodiment also contains distal pressure hole 164 and proximal pressure hole 163 along with a balloon 166. The operation of the catheter shown in FIG. 10 is similar to that for FIG. 8, above, using an internal guide wire to straighten the catheter on insertion with the guide wire being retracted when the catheter is desired to be fixed in place.

The catheter of the present invention allows one to simultaneously measure instantaneous volumetric flow, blood vessel diameter, instantaneous velocity profile and pulmonary artery pressure and/or pulmonary capillary wedge pressure. This combination of hemodynamic parameters will allow a physician to obtain a more accurate assessment of the patient's cardiovascular state at any time and the changes in such state with various physiological and pharmacological interventions. Mapping of the velocity profile of the major blood vessel may also provide the physician with a better understanding of the basic disease processes of these vessels and the heart in general.

What is claimed is:

1. A catheter for making measurements in a vessel defined by a wall carrying a fluid, comprising an elongate flexible tubular member having a plurality of lumens extending therethrough and having proximal and distal extremities, an inflatable balloon carried by the distal extremity of the tubular member and having the interior of the balloon in communication with one of the lumens in the flexible tubular member, the tubular member having at least one preformed bend therein adjacent the distal extremity of the tubular member, a transducer carried by the tubular member in the region of the preformed band, conductive means connected to the transducer and carried by the tubular member and extending through one of the lumens in the tubular member to the proximal extremity of the tubular member, the tubular member having an opening in the distal extremity distal of the balloon in communication with one of the lumens in the tubular member, the tubular member having another opening proximal of the balloon and in communication with another lumen and straightening means carried by the tubular member for straightening the preformed end when it is extended through the preformed bend to facilitate insertion of the catheter into the vessel and for permitting the tubular member to assume the preformed bend with the vessel when it is retracted so that it does not extend through the preformed bend so that a portion of the preformed bend is urged toward the wall of the vessel to position the transducer so that radiation emitted thereby passes through the fluid in the vessel.

2. A catheter as in claim 1 wherein said tubular member has at least two preformed bends therein.

3. A catheter as in claim 1 wherein said means carried by the tubular member for straightening the preformed bend comprises a straightening wire, the straightening wire having a distal extremity with a tapered portion, a coil spring secured to the distal extremity of the straightening wire and a rounded protrusion carried by the distal extremity of the coil spring.

4. A catheter as in claim 3 wherein the straightening wire in an extended position extends through one of the lumens in the tubular member beyond the preformed bend and in a retracted position does not extend through the preformed bend.

5. A catheter as in claim 1 wherein the transducer is positioned in the tubular member so that it faces outwardly through the opening proximal of the balloon.

6. A catheter as in claim 1 wherein said tubular member is provided with an additional opening proximal of the said another opening and in communication with another lumen.

7. A catheter as in claim 6 wherein said additional opening is spaced from said another opening by approximately five centimeters.

8. A method for making measurements in a vessel defined by a wall and carrying a fluid by the use of a catheter having a preformed bend therein and having a transducer positioned in the catheter in the vicinity of the preformed bend, comprising the steps of straightening the catheter so that the preformed bend is substantially removed therefrom, inserting the catheter into the vessel, permitting the catheter to assume its preformed bend after being introduced into the vessel to permit at least a portion of the bend to engage the wall of the vessel so that the transducer is positioned in a predetermined manner so that radiation emitted by the transducer passes through the fluid in the vessel, making measurements with the transducer, straightening the catheter so that the bend is substantially removed therefrom and removing the catheter from the vessel.

9. A method as in claim 8 wherein the transducer is positioned so that the radiation emitted from the transducer passes through the central axis of the vessel.

10. A method as in claim 8 wherein the vessel is the pulmonary artery of a human heart and wherein the catheter is provided with a transducer lumen slot adjacent the transducer and a right ventricular hole proximal of the transducer slot by approximately five centimeters together with the step of ascertaining when the transducer is in the main pulmonary artery by simultaneously observing pulmonary artery pressure in the transducer lumen slot and the lack of pulmonary artery pressure in the right ventricular hole.

* * * * *

UNITED STATES PATENT AND TRADEMARK OFFICE
CERTIFICATE OF CORRECTION

PATENT NO. : 4,856,529
DATED : August 15, 1989
INVENTOR(S) : Jerome Segal

It is certified that error appears in the above-identified patent and that said Letters Patent is corrected as shown below:

ON TITLE PAGE:
In the Abstract, line 25, after "within", delete [in]

Col. 2, line 43, after "member", insert --.--

Col. 3, line 32, delete [the]
Col. 4, line 66, delete [0.01] and substitute --0.0012--
Col. 4, line 68, delete [0.0012] and substitute --0.01--
Col. 5, line 3, insert --outside-- before diameter, delete [0.005] and substitute --0.05--
Col. 7, line 26, delete [0.15] and substitute --1.5--
Col. 9, line 19, delete [vessel] and substitute --vessels--
Col. 9, line 35, delete [band] and substitute --bend--
Col. 9, line 46, delete [end] and substitute --bend--

Signed and Sealed this

Tenth Day of September, 1991

*Attest:*

HARRY F. MANBECK, JR.

*Attesting Officer*     *Commissioner of Patents and Trademarks*